United States Patent
Carpentier et al.

(10) Patent No.: US 8,977,361 B2
(45) Date of Patent: Mar. 10, 2015

(54) APPARATUS FOR THE TREATMENT OF BRAIN AFFECTIONS AND METHOD IMPLEMENTING THEREOF

(75) Inventors: Alexandre Carpentier, Paris (FR); Cyril Lafon, Toussieu (FR); Jean-Yves Chapelon, Villeurbanne (FR); Michael Sean Canney, Lyons (FR); Kévin Beccaria, Paris (FR)

(73) Assignees: Universite Pierre et Marie Curie (Paris 6), Paris Cedex (FR); Assistance Publique—Hopitaux de Paris, Paris (FR); Carthera, Paris Cedex (FR)

( * ) Notice: Subject to any disclaimer, the term of this patent is extended or adjusted under 35 U.S.C. 154(b) by 24 days.

(21) Appl. No.: 13/577,938

(22) PCT Filed: Feb. 22, 2011

(86) PCT No.: PCT/EP2011/052611
§ 371 (c)(1),
(2), (4) Date: Mar. 25, 2013

(87) PCT Pub. No.: WO2011/101492
PCT Pub. Date: Aug. 25, 2011

(65) Prior Publication Data
US 2013/0204316 A1    Aug. 8, 2013

(30) Foreign Application Priority Data
Feb. 22, 2010   (EP) .................. PCT/EP2010/052206

(51) Int. Cl.
*A61N 1/00*   (2006.01)
*A61N 1/36*   (2006.01)
(Continued)

(52) U.S. Cl.
CPC ............ *A61N 1/3606* (2013.01); *A61N 5/0601* (2013.01); *A61N 7/02* (2013.01);
(Continued)

(58) Field of Classification Search
CPC .... A61N 1/3605; A61N 1/36082; A61N 1/36
USPC ......................................... 607/45
See application file for complete search history.

(56) References Cited

U.S. PATENT DOCUMENTS 5,524,624 A    6/1996   Tepper et al.
6,248,126 B1   6/2001   Lesser et al.
(Continued)

FOREIGN PATENT DOCUMENTS

EP   1 834 646   9/2007
EP   1 894 090   3/2008
(Continued)

*Primary Examiner* — George Manuel
(74) *Attorney, Agent, or Firm* — Clark & Brody

(57) ABSTRACT

The present invention relates to an apparatus for the treatment of a brain affection, which comprises at least one implantable generator (4) made of non-ferromagnetic material comprising a casing (7), an ultrasound generating treating device (11) positioned into said casing to induce brain affection treatment by emission of ultrasound waves, and means for fastening the implantable casing into the skull. The apparatus further comprises a power controller (PwC) to supply electricity to the treating device of the implantable generator and to set and control its working parameters, and connecting means (6) to connect the power controller and the treating device of the implantable generator. A method for treating a brain affection with such an apparatus is also disclosed.

35 Claims, 6 Drawing Sheets

(51) Int. Cl.
*A61N 5/06* (2006.01)
*A61N 7/02* (2006.01)
*A61B 8/08* (2006.01)
*A61N 7/00* (2006.01)

(52) U.S. Cl.
CPC ...... *A61B 8/0816* (2013.01); *A61N 2005/0651* (2013.01); *A61N 2007/0021* (2013.01); *A61N 2007/0052* (2013.01); *A61N 2007/0078* (2013.01); *A61N 2007/025* (2013.01)
USPC .......................................................... 607/45

(56) References Cited

U.S. PATENT DOCUMENTS

| | | | |
|---|---|---|---|
| 6,321,104 B1 | 11/2001 | Gielen et al. | |
| 6,862,479 B1* | 3/2005 | Whitehurst et al. | 607/39 |
| 7,302,298 B2 | 11/2007 | Lowry et al. | |
| 7,421,297 B2 | 9/2008 | Giftakis et al. | |
| 7,717,853 B2 | 5/2010 | Nita | |
| 7,819,812 B2* | 10/2010 | John et al. | 600/504 |
| 7,949,401 B2 | 5/2011 | Fowler et al. | |
| 2003/0225331 A1 | 12/2003 | Diederich et al. | |
| 2004/0267234 A1 | 12/2004 | Heart et al. | |
| 2005/0015128 A1 | 1/2005 | Rezai et al. | |
| 2005/0283203 A1 | 12/2005 | Flaherty et al. | |
| 2006/0058708 A1 | 3/2006 | Heart et al. | |
| 2007/0016040 A1 | 1/2007 | Nita | |
| 2007/0038100 A1* | 2/2007 | Nita | 600/439 |
| 2007/0129652 A1 | 6/2007 | Nita | |
| 2007/0225773 A1 | 9/2007 | Shen et al. | |
| 2007/0299370 A1 | 12/2007 | Bystritsky | |
| 2008/0004676 A1 | 1/2008 | Osypka et al. | |
| 2008/0039895 A1 | 2/2008 | Fowler et al. | |
| 2008/0195160 A1 | 8/2008 | Wingeier et al. | |
| 2008/0275526 A1 | 11/2008 | Lozano | |
| 2009/0112278 A1 | 4/2009 | Wingeier et al. | |
| 2009/0222067 A1 | 9/2009 | Toselli et al. | |
| 2009/0254134 A1 | 10/2009 | Nikolov et al. | |
| 2010/0002275 A9 | 1/2010 | Argoitia et al. | |

FOREIGN PATENT DOCUMENTS

| | | |
|---|---|---|
| JP | 2001-327495 | 11/2001 |
| JP | 2003-325616 | 11/2003 |
| WO | 2006/042163 | 4/2006 |
| WO | 2006/092061 | 9/2006 |
| WO | 2007/064453 | 6/2007 |
| WO | 2009/067323 | 5/2009 |
| WO | 2009/132855 | 11/2009 |

* cited by examiner

APPARATUS FOR THE TREATMENT OF BRAIN AFFECTIONS AND METHOD IMPLEMENTING THEREOF

TECHNICAL FIELD

The present invention relates to an apparatus and a method for the treatment of brain affections like brain tumors as well as brain diseases and brain disorders like Alzheimer disease or Parkinson disease.

BACKGROUND ART

In the last decades, the academic and clinical knowledge and understanding of brain processes and diseases have considerably improved and so have the medical and surgical treatments of such pathologies. One field of brain medicine which has particularly developed is the field of neuromodulation techniques, which consist in submitting brain areas to a physical stimulation like an electric current or a magnetic field to treat a neurological disorder. Among neuromodulation techniques, DBS (which stands for "Deep Brain Stimulation") with electrical probes, TES (which stands for "Transcranial Electrical Stimulation") and TMS (for "Transcranial Magnetic Stimulation") are well known and exemplified in literature.

Recently, it has been proposed in WO 2006/092061 A1 implantable devices to cause lasting changes in neural functions through several types of physical stimulation (mechanical impulsion on cortex, electrical deep brain stimulation, drug infusion, for neurological deficit rehabilitation). It has also been suggested in WO 2009/067323 A1 devices for creating a skull/brain interface, which devices (implantable into the skull) are totally passive windows or channels permeable to external physical means (electric ionic current, radiofrequency . . . ) in order to neuromodulate brain activity for movement disorder or epilepsy pathologies.

In the field of brain cancer treatment, such neurostimulation techniques are not efficient. The treatments applied to this pathology remain the same as those applied for any kind of cancer, i.e. chemotherapies and/or surgical ablation of tumors when it is possible without irreversible or lethal damaging of the brain.

Surgical treatments of the brain require open surgical procedures in the skull of patients. Such open surgical procedures comprise a craniotomy, which includes performing a bone flap.

To do so, the surgeon firstly performs a trepanation in the skull by piercing several burr holes, and secondly unsticks the durra matter underneath. After that, the surgeon then performs the craniotomy by using a saw going from one burr hole to the other. Burr holes are usually 10 to 12 mm diameter each. The fragmented bone chip of each burr hole is kept and used at the end of the surgery to fill bone defects, which suffer poor, long-term, ossification. At the end of the surgical procedure, the bone flap is repositioned and fixed either with trans-skull stitches or with titanium micro-plates. The bone defect areas are filled up either with a synthetic copolymer or with bone powder obtained from the drilling of the burr holes at the beginning of the procedure.

These craniotomy procedures are heavy to support for the patients and leave irreversible traumas in the skull.

Ultra keyhole surgical procedures do not require performing a bone flap, but only a burr hole. This burr hole can be very slight (4 mm diameter) in cases of stereotactic biopsy, but can be larger (between 8 to 12 mm diameter) for endoscopic procedures required for partial ablation of tumors.

Where chemotherapeutic treatments are concerned, these treatments include administration of highly active drugs to the patients. Unfortunately, these drugs are not specifically active onto the tumors and they also have considerable negative effects in the whole body of patients, with very unpleasant side-effects like nausea, hair loss etc. . . . .

For some years now, high intensity ultrasounds have shown to be a relevant physical mean to treat tumors by their capacities to thermo coagulate the tissue (high intensity ultrasounds). However, in the brain, such ultrasound treatments are by now ineffective due to the skull barrier that absorbs and diffracts ultrasounds waves.

SUMMARY OF THE INVENTION

The present invention aims at providing a new treatment for brain tumors and other brain disorders.

The invention particularly aims at providing a less traumatic method and device for the treatment of brain tumors and/or disorders.

Another goal of the invention further focuses on providing a treatment for brain tumors and disorders, which can precisely be active at the tumors' locations in the brain with no or limited effects on the rest of the brain or body of the patient.

According to a first aspect, the invention proposes an apparatus for the treatment of a brain affection, in particular a brain tumor, characterized in that it comprises at least one MRI compatible implantable generator made of non-ferromagnetic material for implantation into a burr hole performed in the skull of a patient, said implantable generator comprising:
  a casing having at least an upper wall, and a lower wall connected together by a peripheral wall,
  an ultrasound generating treating device positioned into said casing to induce brain affection treatment by emission of ultrasound waves through its lower wall into the brain, and
  means for fastening the implantable casing into the skull, said apparatus further comprising:
  a power controller to supply electricity to the treating device of the implantable generator and to set and control its working parameters, and
  connecting means to connect the power controller and the treating device of the implantable generator.

The apparatus according to the invention is dedicated to the treatment of brain diseases and disorders by emission of ultrasound waves with the treating device of the apparatus of the invention directly into the brain. The ultrasound waves are emitted with the treating device at a chosen frequency and can be focused onto a determined area of the brain to specifically and locally treat that area.

Advantageously, the implantable generator is designed as MRI compatible, i.e. made of non-ferromagnetic materials, to guaranty MRI compatibility and prevent MRI signal artefact and diffraction. Preferably, said implantable generator is made of an isolating polymer material.

According to the invention, the power controller is adapted for the treating device to emit ultrasound waves with an emission frequency of between 200 kHz and 10 MHz, and preferably 1 MHz.

To emit ultrasound waves into the brain the treating device comprises at least one ultrasound transducer. Preferably, the treating device comprises at least one highly efficient ultrasound transducer such as a High-Intensity Focused Ultrasound (HIFU) ultrasound transducer.

According to another feature of the apparatus of the invention, the at least one ultrasound transducer comprises elements chosen into the group formed by: piezo-composite elements, piezo-ceramic elements, capacitive ultrasonic elements (C-MUT elements), or polyvinylidene difluoride (PVDF) elements.

In another embodiment, the apparatus of the invention further comprises beam steering elements to direct propagation of the ultrasound waves in the brain to a targeted area or location. Such beam steering of the emitted ultrasound waves proves particularly advantageous to target different brain areas from one single burr-hole location for the implantable generator of the apparatus of the invention.

Preferably, the beam steering elements comprise phase difference inducing electrical components implemented in the power controller and/or the treating device, which are preferably integrated or associated to the ultrasound transducers of the treating device. Such phase difference inducing components can for instance comprise filters, capacitors and combinations thereof.

In an alternative embodiment of the apparatus of the invention, the treating device further comprises at least one light emitter, such as at least one electroluminescent diode, preferably in addition to said transducer(s).

The apparatus of the invention is designed for treating brain affections by means of ultrasounds and/or light emissions into an area of the brain where treatment is required. To ease emission and diffusion of the ultrasounds and/or light into the brain, the lower wall of the implantable casing of the apparatus is advantageously permeable to ultrasound waves and to light.

Preferably, the lower wall of the implantable casing also comprises or defines at least one lens assembly for focusing or defocusing the ultrasound waves emitted into the brain.

Still preferably, the at least one lens assembly is advantageously displaceable about a longitudinal axis of the casing to allow adjustment of the focal length of the ultrasound and/or light waves into the brain.

In another embodiment of the apparatus of the invention, the lower wall of the casing comprises an external surface covered with a soft material of variable thickness to provide a continuous interface with the brain or dura-matter in the skull for the propagation of ultrasound waves into the brain.

In an advantageous embodiment, the apparatus of the invention further comprises detection elements for receiving and analysing ultrasound waves reflected by the brain, also called backscattered waves, or, more specifically, reflected by contrast agents diffused in the brain's blood. Such detection elements preferably comprise ultrasound transducers, either specifically dedicated to the reception and treatment of the reflected waves or emitting ultrasound transducers of the treating device set in a receiving mode. In both cases, the ultrasound elements are connected directly to the power controller for treatment of the electric signal derived from the reflected waves.

According to another characteristic of the apparatus of the invention, said implantable generator comprises connecting plugs to accommodate the connecting means and ensure connection between the power controller and the treating device.

In an advantageous embodiment of the invention, the connecting plugs are transdermic plugs held into the upper wall of the casing of the implantable generator and comprise an isolating coating preventing contact with the patient's skin.

Preferably, the connecting means comprises transdermic needles suitable for plugging into the connecting plugs through the patient's skin, said transdermic needles being coated with an isolating material except at their tip for contacting the treating device connectors through the connecting plugs.

The use of transdermic needles as electrical connections between the power controller and the implantable generator avoids MRI incompatibility issues of the apparatus of the invention. The implanted patient can be easily disconnected from the power controller to follow MRI tests during or after treatment.

According to an alternative embodiment of the invention, said power controller and said connecting means are implemented into said casing and said power controller comprises wireless programmable means, for instance radiofrequency communication means or, preferably, ultrasound communication means.

The use of ultrasound communication means proves particularly advantageous for setting and monitoring the treating device during MRI acquisitions.

The apparatus then also comprise advantageously a transcutaneous wireless remote control for programming and setting said wireless programmable means, said remote control implementing adequate wireless programmable means such as RF means or preferably ultrasound means.

In another embodiment of the invention, the apparatus comprises multiplexing means for controlling and setting the treating device. Said multiplexing means comprises at least a first multiplexing calculator embedded into said power controller, at least one communication bus for digital signal transmission between said power controller and the treating device and at least a second multiplexing calculator embedded into said treating device to receive and convert the digital signal from the power controller into an analogic signal usable by the treating device.

In a further variant embodiment of the apparatus of the invention, the apparatus of the invention is miniaturized and the power controller is advantageously implemented onto an electronic card or an integrated circuit. In that miniaturized embodiment, the power controller is inserted within the casing lodging the treating device and connected to that treating device to command it.

Electrical supply for the power controller and the treating device is then provided either by an extraneous generator connected to the connecting plugs or, as an alternative, by a subcutaneous battery implanted in the thoracic region like usually carried out in heart surgery. Such a battery can advantageously be charged by the ultrasound communication means potentially used as wireless communication means.

In such a miniaturized embodiment, multiplexing communication can also been arranged for the power controller and treating device with adapted miniaturized digital calculators and communication buses, for instance embedded onto an electronic card receiving the power controller. Control of the multiplexing can then be carried out by radiofrequency modulation with an external emitter, a computer or the like.

As a complementary feature of the invention, the fastening means of the casing preferably comprises tabs formed on the edge of the upper wall of said casing, the tabs comprising screw holes for receiving anchoring screws.

In an alternative embodiment, said fastening means preferably comprises a screwing thread on an external surface of the peripheral wall of the casing for said casing to be screwed manually in a burr-hole in the skull.

According to a second aspect, the invention also relates to a method for treating brain affections, characterized in that it comprises the steps of:
  performing at least one burr hole into the skull of a patient,
  implanting into said at least one burr hole an implantable generator of an apparatus as previously described,
  surgically close the skin and let it heal when needed for a treatment procedure, activating the implantable generator and the power controller of the implanted apparatus, supplying power to said generator to activate the treating device of said generator and induce ultrasound waves emission into the brain, treating an area of the brain located beneath the implantable generator by ultrasound waves emission into the brain during a determined period, and deactivating the treating device when treatment is complete.

The method of the invention can be carried out at the end of a traditional neurosurgical procedure. The implantable generator is introduced in a burr hole performed in the skull of a patient or, when needed, in holes performed for a craniotomy procedure just before the skin closure of the patient. Such generator emit physical waves such as ultrasound waves for treating the brain and specifically an area of the brain previously accessed by the surgeon to treat a brain pathology, and for example a brain tumor.

However, tumors treatment is not the only application of the apparatus and method of the present invention. Indeed, ultrasound technology offers a very broad spectrum of medical applications, which can be carried out together or alternatively with the method of the present invention. These complementary applications encompass:

Measuring intracranial physiological parameters like intracranial blood pressure, temperature, tissue elasticity . . . ;

Echography imaging (normal, Doppler, shear modes);

Electrophysiological activation or inhibition;

Hyperthermia for enhancing blood vascularization and the enhanced permeability retention effect;

Opening of the haematoencephalic barrier by ultrasonic activation of ultrasound sensitive contrast agents;

Thermal necrosis of tissues through intense and focused hyperthermia;

Tumor fragmentation by low frequency ultrasound emission; and

Combinations of any of the above described applications in the method of the invention with simultaneous contrast agent injection.

It can be used either in a thermal destruction way, particularly for tumor treatment but also at a lower energy to modulate cerebral activities in the case of brain disorder pathologies.

According to the method of the invention, the ultrasound waves emitted in the brain can be focused or non-focused waves transmitted to the brain for treating brain affections.

The emission of ultrasound waves in the method of the present invention proves particularly efficient in the treatment of tumors, which forms a first prominent application of said method. The generator and its treating device being implanted into the patient's skull, the ultrasounds emitted in the brain are not absorbed nor diffracted by the cranial bone wall. When the generator of the apparatus of the invention has been inserted in the skull the lower wall of the casing accommodating the treating device directly faces the brain. Consequently, the ultrasound waves emitted by said treating device according to the inventive method of the invention are directed and diffused directly through the brain for direct treatment.

With respect to the first embodiment of the invention previously presented the method of the invention preferably further includes injecting at least one contrast agent in the patient's blood before or during ultrasound waves' emission to trigger and/or enhance opening of the haematoencephalic barrier of the treated brain.

According to another advantageous characteristic of the invention, the method further comprises a step of intravenously injecting a drug in the blood of a patient before or during ultrasound emission in the brain, said drug comprising therapeutic agents coated with ultrasound sensitive release or carrier agents, and then emitting ultrasound waves with the implantable generator into the brain once the drug treatment has diffused in the patient's blood to release the therapeutic agents only into the area of the brain to be treated.

In cases of tumor lesions, intravenous systemic chemotherapy is usually administered after surgery with products like Temodal (Registered Trademark) or Avastin (Registered Trademark). Such drugs have systemic undesirable consequences.

Instead of administering those drugs intravenously in the whole organism, the method of the invention proposes coating such drug with ultrasound sensitive release agents so that the drug can be released only when it enters the ultrasound field emission. By this mean, the active drug is only released in the brain area to be treated and doesn't affect the rest of the organism.

The drug injected is preferably MRI-visible so that its release within the brain can be monitored by MRI during or after the ultrasound emission treatment performed according to the method of the invention.

The possibility foreseen by the method of the invention of using an ultrasound emission together with an ultrasound sensitive drug release agent or carrier (i.e. nanoparticles) is real breakthrough in the field of brain affection treatments as it allows for the first time to reduce the shortcomings and side-effects of usual drug chemotherapeutic treatments. Indeed, ultrasound emission induces a loco regional release of drugs coated or added with ultrasound sensible release agents such as nanoparticles or liposomes for example.

According to the method of the invention the ultrasound waves emission and injections of contrast agent(s) and/or drug(s) can furthermore advantageously be monitored and synchronized by means of the power controller of the apparatus of the invention. Thanks to such monitoring and synchronization, the delivery of both drug(s) and ultrasounds to the area to be treated in the brain can be efficiently controlled, for example under MRI acquisition, so as to accurately target the appropriate brain area for the shortest possible time, thereby ensuring efficiency of treatment together with preservation of the peripheral tissues.

Moreover, the implementation of ultrasound waves directly within the brain according to the invention allows definitive or reversible sonoporation of the underneath cerebral tissue to increase drug input.

Another advantage of the method of the invention relates to the possibility of modification of electrophysiological brain activity by mechanical shear stress, through ultrasound emission for the treatment of specific brain disorders or diseases. For example, a loco regional sono-destruction or decomposition of pathological abnormal molecular deposit can be carried out by ultrasound emission according to the method of the invention for the treatment of Alzheimer disease patients.

As a complementary measure in the method of the invention the implantable generator may comprise a light emitting device and focused or non-focused light waves can be transmitted together with ultrasound waves in the brain for treating brain affections. The use of light as a treating stimulus may be advantageous to address some specific diseases or trauma of the brain, which cannot be treated by ultrasounds exclusively.

On a practical approach of the method of the invention, the axis of the burr hole drilled in the patient's skull is preferably directed towards the area to be treated in the brain.

The method of the invention also contemplates drilling several burr holes in the patient's skull, each accommodating an implantable generator, said holes and generators being positioned in a specific fashion, for example concentric fashion, with regard to the area of the brain to be treated. This then helps concentrating the effects of the treatment all around the area to be treated for a better and faster efficiency of the treatment.

Preferably, positioning of the burr hole(s) and implantable generator(s) is carried out in the method of the invention by stereotaxy, for instance at the end of a regular tumor biopsy procedure, by using existing craniotomy burr hole(s).

BRIEF DESCRIPTION OF THE DRAWINGS

The apparatus and method of the present invention will be further described in detail below with reference to the accompanying drawings showing preferred embodiments of the apparatus of the invention.

In the figures.

DESCRIPTION OF EMBODIMENTS

Figure 1:
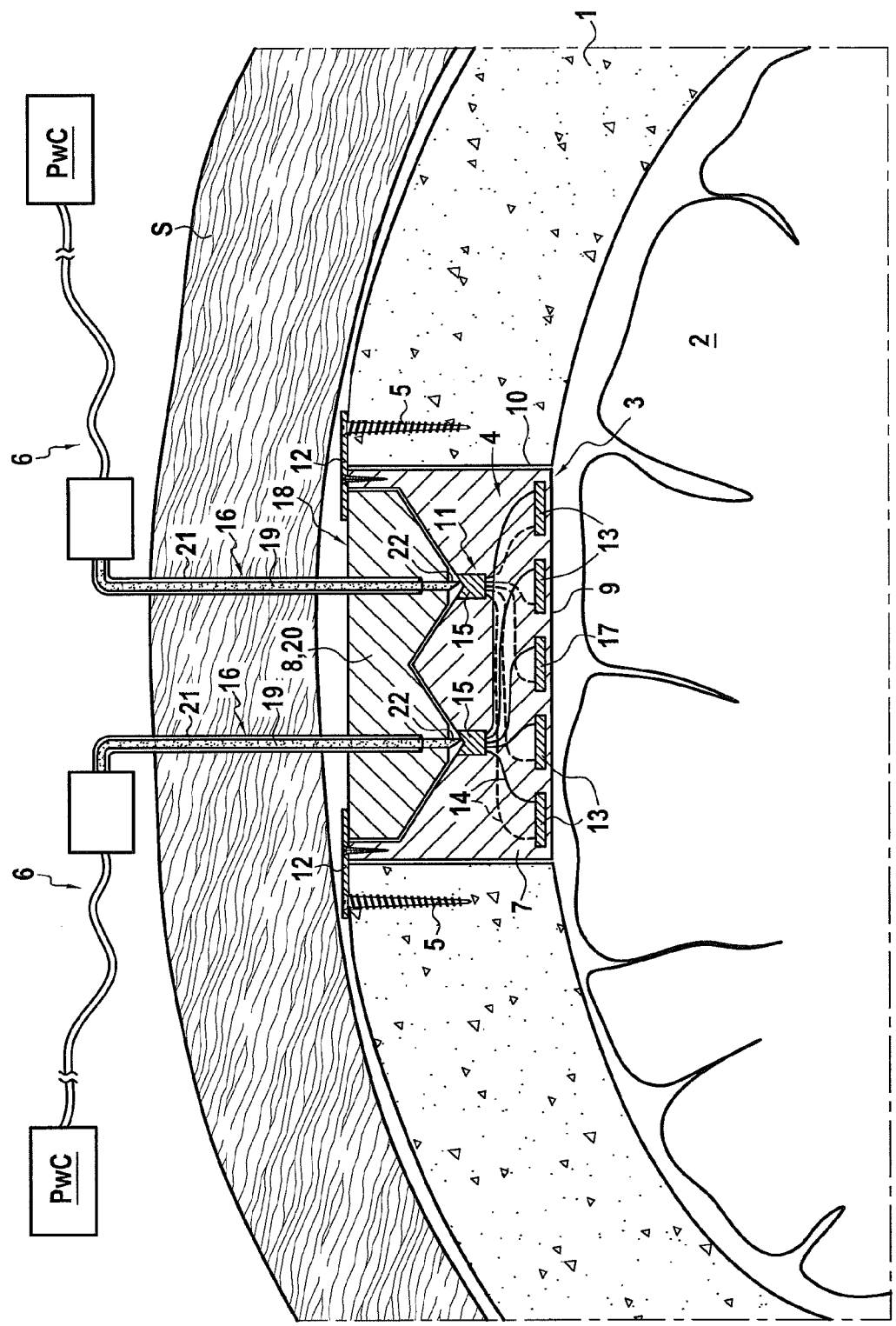
FIG. 1 represents a first embodiment of the apparatus of the present invention.

The enclosed FIG. 1 is a section view of a human skull 1 covering the brain 2 and into which a burr hole 3 has been drilled to perform a regular craniotomy.

The burr hole 3 receives an implantable generator 4 fastened to the skull 1 by means of bone screws 5. The implantable generator 4 is part of an apparatus for the treatment of brain affections, which also comprises an extraneous power controller PwC to supply electricity and command signals to the implantable generator 4 and to set its working parameters, and connecting means 6 to connect the power controller PwC and the implantable generator 4.

The implantable generator 4 is formed of a casing 7 made of a MRI compatible non-ferromagnetic material biocompatible material such as plastic, preferably in a cylinder shape. Said casing 7 comprises an upper wall 8 and a lower wall 9 connected by a circular peripheral wall 10.

The cylindrical casing 7 accommodates a treating device 11 designed for emitting physical waves directly into the brain 2 through the lower wall 9 of the casing 7 to induce brain affection treatment. The casing 7 advantageously comprises fastening means for the implantable generator 4.

In the embodiment shown in FIG. 1 the fastening means may consist in peripheral tabs 12 with hole(s) for receiving the bone screws 5 to fix the implantable generator 4 to the skull 1.

Figure 2:
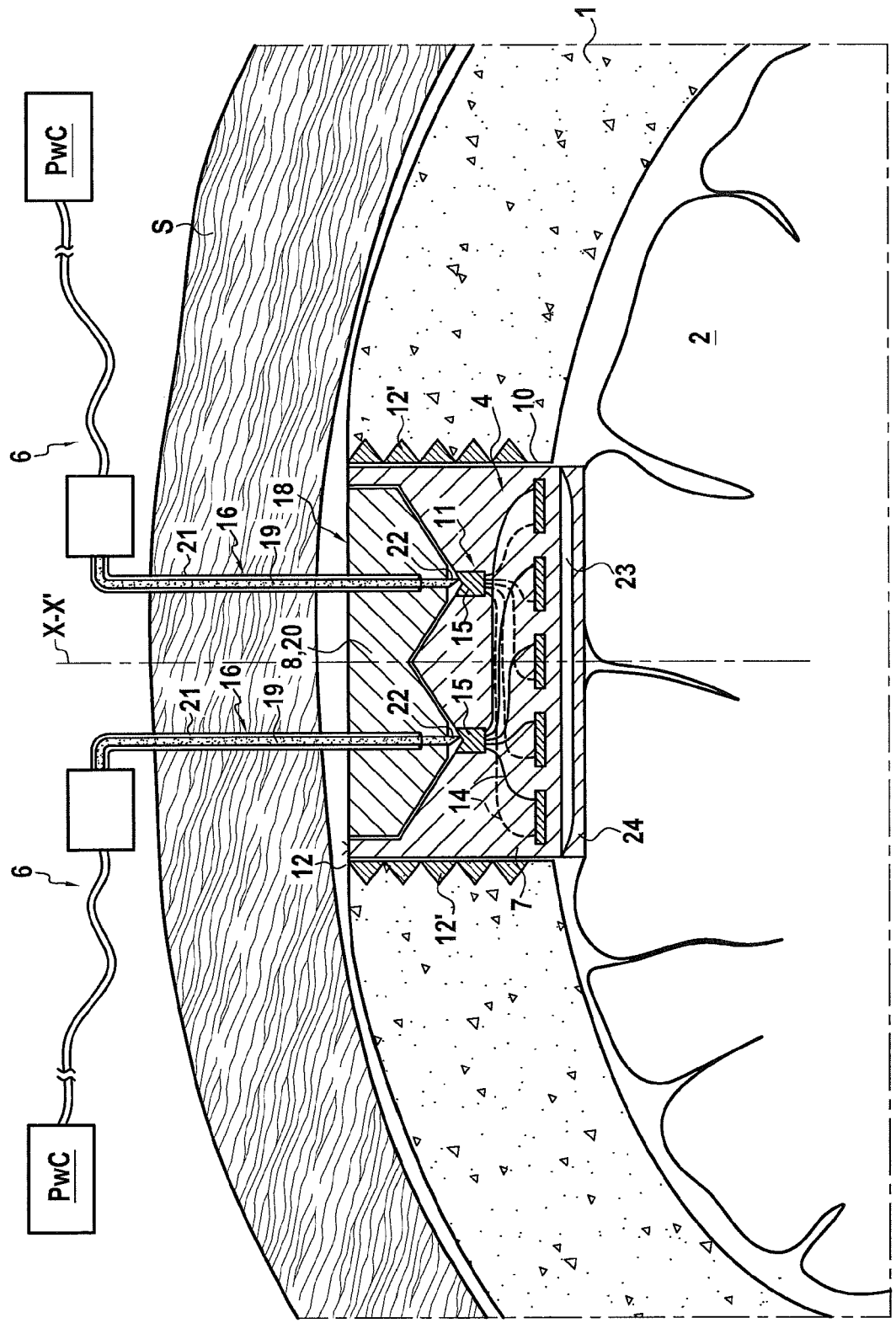
FIG. 2 represents a second embodiment of the apparatus of the present invention.

In a variant embodiment shown in FIG. 2, the fastening means may consist in a peripheral external screwing thread 12' formed on the external surface of the peripheral wall 10 of the casing 7. In that embodiment, the implantable generator 4 can advantageously be screwed manually in the burr-hole 3 by a surgeon.

While FIG. 2 shows an embodiment of the apparatus of the invention where the fastening means consists in an external screwing thread 12' it should be considered that such fastening means are not limited to the embodiment in FIG. 2 and could also be all the same implemented in the embodiments of the apparatus 1 shown in FIG. 1 and FIGS. 3 to 5 which all show fastening means in the form of peripheral tabs 12 receiving screws 5.

It is a very important characteristic of the present invention that said implantable generator 4 is in its entirety made of non ferromagnetic material to insure MRI compatibility and to prevent MRI signal artefact and diffraction.

The treating device 11 located in the casing 7 comprises means for emitting high intensity physical waves into the brain through the lower wall 9 of the casing when the implantable generator 4 has been positioned in the burr hole 3 in the skull 1.

As shown in FIG. 1 to 5, the treating device 11 preferably consists in an ultrasound generator comprising at least one, and preferably several therapy ultrasound transducers 13 applied onto the inner face of the lower wall 9 of the casing 7 of the implantable generator 4, said therapy ultrasound transducers 13 being connected by wires 14 to connecting plugs 15 fixed to the upper wall 8 of the casing 7 and into which power supply connectors 16 of the power controller PwC can fit.

According to the invention, the therapy ultrasound transducers 13 are preferably chosen into the group formed by piezo-composite elements, piezo-ceramic elements, C-MUT elements, or PVDF elements. These piezoelectric components are commonly used in the medical field to realize ultrasound transducers.

The therapy ultrasound transducers 13 and the power controller PwC are configured to allow HIFU (for High Intensity Focused Ultrasound) techniques for the treatment of brains affections, and for instance brain tumors. Such HIFU techniques provide for brain affections the same advantages as for the treatments of other tumors located in the body, i.e. rapid and precise heat treatment and/or ablation of tumorous tissues with limited heat diffusion around the focus point of the ultrasounds.

According to the invention, the power controller PwC is adapted for setting the emission frequency/emission wavelength of the therapy ultrasound transducers 13 and piloting such emission. The emission frequency can be set for example from 1 kHz to 1 THz. Preferably, the power controller PwC is set so that the treating device's therapy transducers 13 emit ultrasound waves at a frequency between 200 kHz and 10 MHz, and preferably about 1 MHz, what corresponds to an emission wavelength comprised between 7.5 μm and 150 nm.

Preferably, the apparatus 1 of the invention also comprises beam steering elements to direct propagation of the ultrasound waves emitted by the therapy ultrasound transducers 13 in the brain 2 to a targeted area or location.

Such beam steering elements comprise phase difference inducing electrical components implemented in the power controller PwC and/or the treating device 11. For a better compactness of the apparatus 1 and more specifically of its treating device 11, the phase difference inducing components are integrated or associated to the therapy ultrasound transducers 13 and therefore not represented in the accompanying Figures. Such phase difference inducing components can for instance comprise filters, capacitors and combinations thereof.

In addition to the therapy ultrasound transducers 13, the ultrasound generator can advantageously comprise at least one imaging ultrasound transducer 17 designed for echo-imaging of the brain 3, said imaging transducer 17 being connected to the power controller PwC to work at a different frequency from the therapy ultrasound transducers 13 and to produce echo-imaging onto a monitor implemented in or connected to the power controller PwC.

The therapy and imaging ultrasound transducers 13, 17 of the implantable generator 4 of the invention are not necessarily plane and they can be curved so as to easily focus the ultrasound waves they emit onto the area of the brain to be treated or imaged. Preferably, the therapy transducers 13 are positioned so that their focusing axes are all merging into a same focusing point, which is located into the imaging plane of the imaging transducer 17.

It is therefore possible with the apparatus of the invention to treat a brain affection by ultrasound emission while in the same time echo-imaging the area of the brain being treated, for example to monitor correct focusing of the therapy ultrasounds emitted by the therapy ultrasound transducers 13.

In the embodiment of the apparatus 1 of the invention shown in FIG. 2, the lower wall of the implantable casing comprises or defines at least one lens assembly 23 for focusing or defocusing the ultrasound waves emitted into the brain.

That lens assembly is advantageously mounted onto the internal surface of the peripheral wall of the casing accommodating the treating device and is displaceable about the longitudinal axis X-X' thereof. In that configuration, the focal length of the ultrasound waves of the therapy ultrasound transducers 13 can be varied to precisely target a specific area of the patient's brain to focus and treat by ultrasound emission.

The external surface of the lower wall of the casing can also further be covered with a soft material 24 of variable thickness to provide a continuous interface with the brain 2 or dura-matter for the propagation of ultrasound waves into the brain. Such a soft material 24 advantageously prevents from diffraction or dissipation or the emitted and/or reflected ultrasound waves emitted and/or received by the therapy and imaging ultrasound transducers 13, 17 of the treating device.

The ultrasound transducers 13, 17 are connected by wires 14 to connecting plugs 15 of the ultrasound generator. These connecting plugs 15 are located within the implantable casing 7 and are adapted to accommodate connecting rods 16 from the power controller PwC to power the ultrasound transducers 13, 17.

According to the invention, the connecting plugs 15 are preferably transdermic plugs held into the upper wall 8 of the casing 7 of the implantable generator 4 and comprise an isolating coating 18 preventing contact with the patient's skin. In addition, the connecting rods 16 are transdermic needles 19. These needles are suitable for piercing the patient's skin and the upper wall 8 of the implantable casing 7 before plugging into the connecting plugs 15 inside the implantable generator 4. The upper wall 8 of the casing 7 is preferably made of an isolating concealable material 20 like Silastic®, from the silicone manufacturer Dow Corning. This material can easily and automatically reseal when the needles are withdrawn from the implantable generator 4. Thus, the upper wall 8 forms a sealing gasket between the treating device 11 in the casing 7 and the biological fluids and tissues of the patient's head.

Advantageously, the transdermic needles 19 are coated with an isolating material 21, for instance wax or plastic on their entire length except at their tip 22 so that an electric contact can be established at their tip within the connecting plugs 15 to power the implantable generator 4 without electric burns in the patient's skin. As represented in the accompanying drawing, the connecting plugs 15 are held within the casing 7 of the implantable generator 4, just beneath the upper wall 8 of the casing, formed by a thick plate of sealing material 18 or by a self-sealing membrane.

The embodiment of the invention represented in FIG. 1 depicts a bipolar connection between the power controller PwC and the implantable generator 4 by two transdermic needles 19. However, unipolar connection by means of a single transdermic needle together with a ground secondary connection is also possible.

Figure 3:
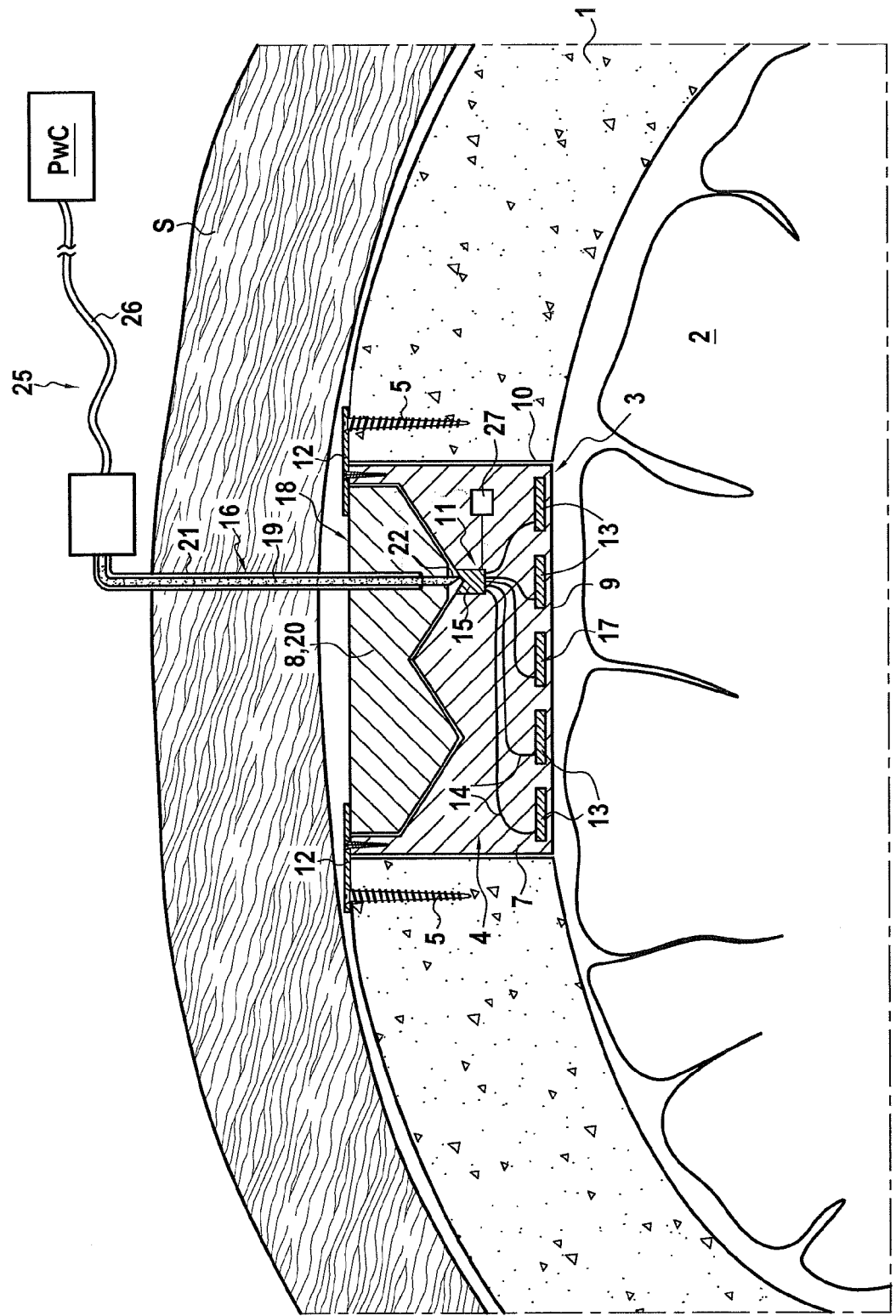
FIG. 3 represents a third embodiment of the apparatus of the present invention.

In a further advantageous embodiment of the invention represented in FIG. 3, the treating device can also be connected and commanded by the power controller PwC including a multiplexing assembly 25. In that embodiment, said multiplexing assembly then preferably comprises at least a first multiplexing calculator embedded into said power controller PwC connected by at least one communication bus 26 for digital signal transmission of the command signal to the treating device of the implantable generator 4, which includes a second multiplexing calculator 27 to receive and convert the digital signal from the power controller PwC into an analogic signal usable by said treating device to drive the ultrasound transducers.

Figure 4:
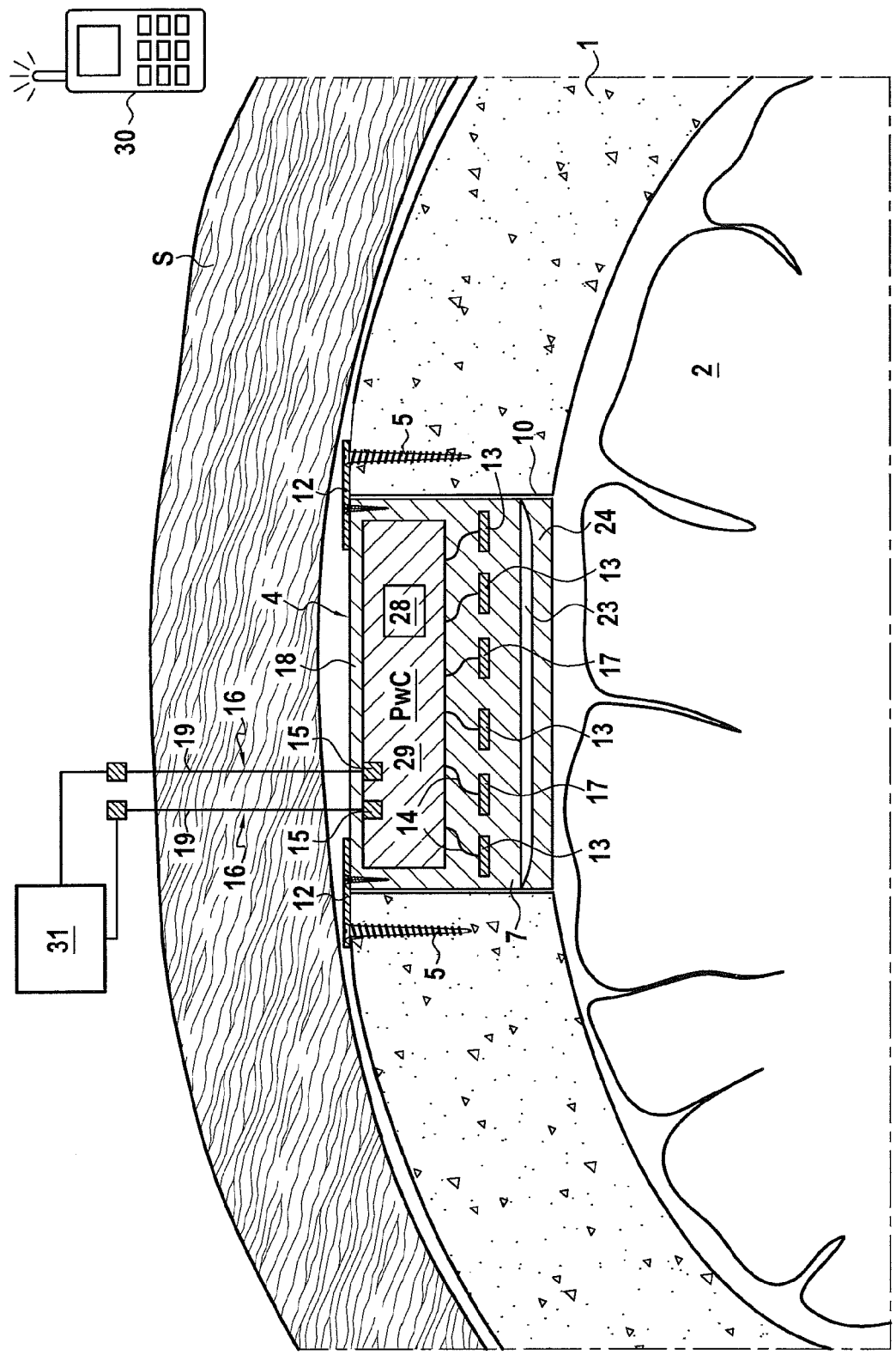
FIG. 4 represents a fourth embodiment of the apparatus of the present invention.

Alternatively, the invention also considers a variant embodiment shown in FIG. 4 into which the power controller PwC and connecting means 6 are not separate from the implantable generator 4 but implemented directly into the casing 7 receiving said generator. To fulfil this design, the power controller PwC then advantageously comprises wireless programmable means 28 and is also preferably implemented onto an electronic card 29 or in the form of an integrated circuit including said wireless communication means to be remotely controlled by an operator, surgeon, doctor, or nurse for example, who sets the working parameters of the implantable generator with an external remote control 30 or computer to perform treatment of the patient's brain by means of a transcutaneous remote control based on radiofrequency for example, or preferably by ultrasound communication means.

Indeed, ultrasound communication means for setting and piloting the power controller and treating device of the apparatus of the invention should be preferred as they are completely MRI compatible. It is thereby possible to contemplate wireless setting and programming of the implantable generator embedding both power controller PwC and treating device under MRI acquisition, so that evaluating directly the working and effects of the apparatus of the invention on a patient's brain following adjustments of the working parameters of the treating device, i.e. ultrasound emission frequency, power, emission duration, . . . etc, before implementing a treatment on a regular basis.

In such a miniaturized embodiment of the apparatus 1 of the invention, electrical supply for the power controller PwC and the treating device can then be provided either by an extraneous generator 31 connected to the connecting plugs of the implantable generator 4 as shown in FIG. 4 or, as an alternative, by a subcutaneous battery implanted in the thoracic region like usually carried out in heart surgery (not shown in the figures). In cases where a battery is used, said battery can advantageously be charged by the ultrasound communication means potentially used as wireless communication means.

Figure 5:
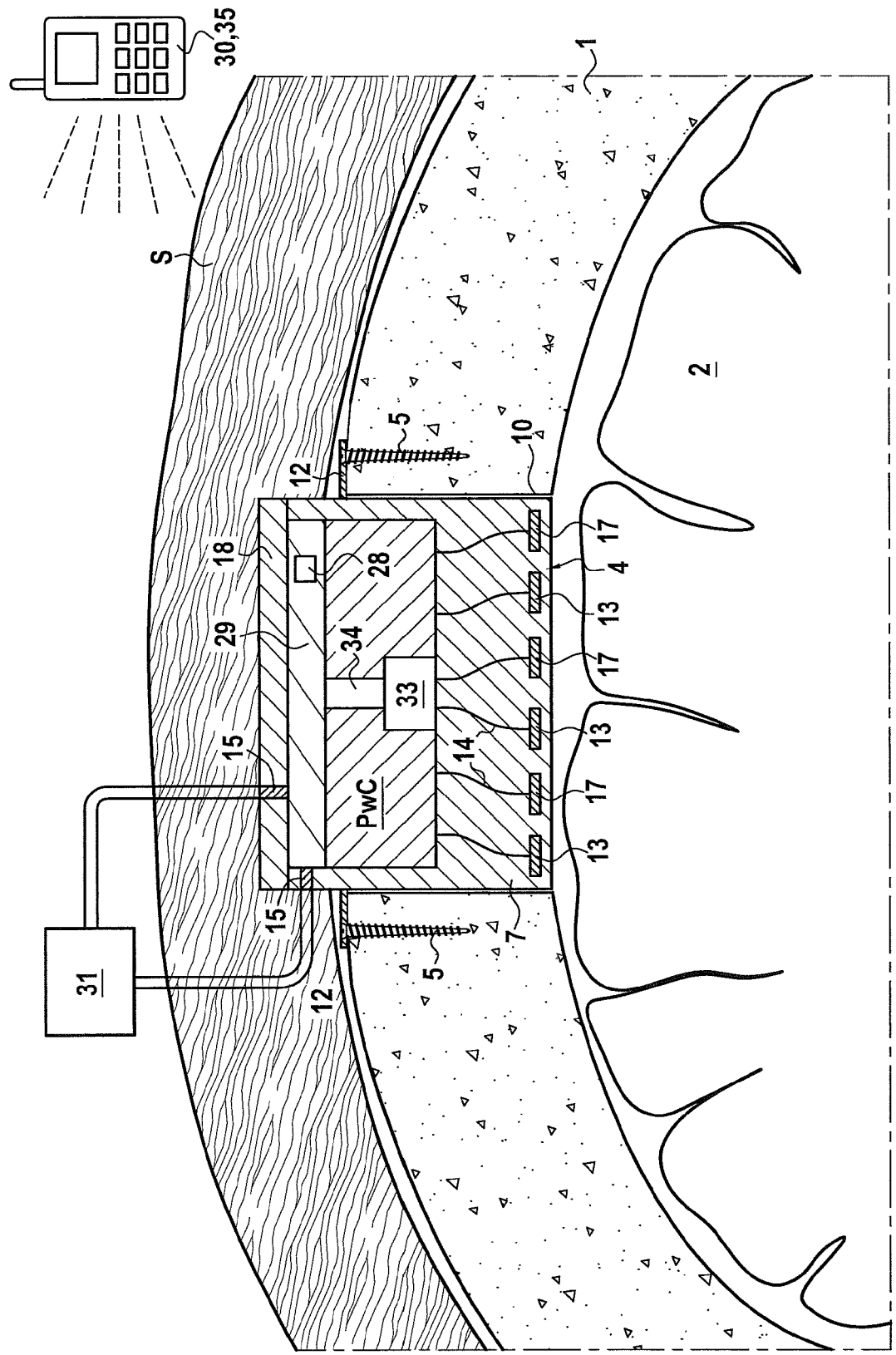
FIG. 5 represents a fifth embodiment of the apparatus of the present invention.

Moreover, as shown in FIG. 5 multiplexing communication can also been arranged for the power controller PwC and treating device with adapted miniaturized digital calculators 32, 33 and communication buses 34, for instance embedded onto the electronic card receiving the power controller PwC. Control of the multiplexing can then be carried out by radiofrequency modulation with an external emitter 35, a computer or the like.

It should be noted that in the present detailed description the apparatus of the invention is described according to a preferred embodiment comprising a treating device located in an implantable casing and comprising ultrasound transducers to emit ultrasound waves into the brain to perform brain affections treatments. However, it can also comprise other active elements working in combination with the ultrasound transducers, and particularly the use of light emission by means, for example, of electroluminescent laser diodes positioned in the implantable generator.

Moreover, it should further be noted that the treating device of the apparatus of the invention might also not be implanted in the skull but only in a subcutaneous manner. However, the frequency emission of the ultrasound waves should then be set lower than 200 kHz to allow passing of the skull bone barrier.

The apparatus 1 of the invention, as described hereinbefore, is aimed at providing a solution for treating brain affections, particularly brain tumors, in complement to regular craniotomies. The apparatus 1 of the invention provides for emission of ultrasound waves, possibly combined with light waves emission, directly in the area of the brain affected.

The invention therefore proposes a complementary method of treatment of such brain affections.

The method of the invention essentially consists in positioning at the end of a traditional neurosurgical procedure (craniotomy debulking or keyhole biopsy) at least one implantable generator 4 of the apparatus previously described in a burr hole 3 practised in a patient's skull 1 just before the skin closure of the patient. Alternatively, it can also be carried out without previous neurosurgical procedure. In that case, burr holes 3 are drilled directly in the patient's skull 1 with the aim of implanting the generators 4 of the apparatus of the invention. The exact positioning of the burr holes 3 to drill in the skull are then preferably determined prior to drilling by stereotaxy.

Once the implantable generator 4 has been implanted in a burr hole 3, it can be secured to the skull 1 on its edges by bone screws 5 introduced in the peripheral tabs 12 of the casing 7 containing the implantable generator 4.

The cranial skin is then sutured over the implantable generator 4 secured in the burr hole 3 and let heal before any further action.

When the skin in the patient's head has heeled, treatment of brain affections can then be carried out. To that aim, the implantable generator 4 is connected to the power controller PwC by means of transdermic needles 19 implanted through the head's skin in the upper wall 8 and connecting plugs 15 of the implantable generator 4, which is power supplied in that way. The treating device 11 in the implantable generator 4 is then activated through the power controller PwC of the apparatus, which the surgeon or practitioner carrying out the treatment has previously set to specific treatment parameters. Once the treating device 11 has been activated, physical waves are thus emitted in the patient's brain 2 to treat the brain area located just beneath the implantable generator 4 in the patient's skull.

Emission of the physical waves in the brain to complete treatment lasts a predetermined time. Once treatment is finished, the practitioner just unplugs the transdermic needles 19 from the implantable generator 4 and the patient's head.

The treatment method of the invention preferably uses ultrasounds as physical waves emitted in the patient's brain. Thus, the treating device 11 of the implantable generator preferably comprises ultrasound transducers capable of emitting, under command of the power controller, ultrasound focused or non focused waves.

Such ultrasound emission in the brain, and specifically in the area of the brain that may have been operated by the surgeon where the pathology was such as tumors, are not absorbed nor diffracted by the skull since they are positioned in the thickness of the skull 1 it self. The effect of ultrasound waves is therefore not affected by the skull and the affected brain area focused can be treated, particularly in the case of brain tumors, like any other organ pathologies already addressed by ultrasound therapy today, with corresponding effects.

The method of the invention thus allows local ablation of tissues, for instance tumorous tissues of the brain 2. It can also induce modification of electrophysiological brain activity by mechanical shear stress, sonoporation, or hyperthermia by ultrasound emission, or a loco regional sono destruction/decomposition of pathological abnormal molecular deposit.

To enhance penetration and efficiency of the ultrasound treatment it is also preferable according to the present invention to inject in the patient's blood at least one contrast agent prior to or during the emission of ultrasounds with the treating device of the apparatus. The injection of such contrast agent surprisingly and advantageously helps and promotes opening of the haematoencephalic barrier of the brain, what enhances diffusion of the ultrasounds within the brain tissues.

The injection of contrast agent(s) can further be combined with an injection of other active products like nanoparticles and/or drugs effective in the treatment of brain pathology.

In cases of tumor lesions, intravenous systemic chemotherapy is usually administered after surgery. Such drugs have systemic undesirable consequences for the patients and have poor intracerebral biodisponibility due to the blood brain barrier.

To reduce these undesirable effects, the method of the invention further includes the step of intravenously injecting a drug in the blood of a patient before or during ultrasound emission in the brain, said drug comprising therapeutic agents coated with ultrasound sensitive release/carrier agents. In that way, the active drug is only released in the organism, and precisely only where the brain affection to be treated is located when ultrasound waves transmitted with the implantable generator 4 into the brain reach encounter the coated therapeutic agents which have diffused in the patient's blood. By this mean, the active drug is only released in the tumor region and doesn't affect the rest of the organism.

The apparatus and method of the invention advantageously allow monitoring and synchronisation, for example by means of the power controller PwC of the apparatus 1 of the ultrasound and, potentially, light waves emission and injection of contrast agent(s) and/or drug(s) into the patient's blood. An example of a combined treatment sequence including injections of a contrast agent A and chemotherapeutic drug B together with non-focused ultrasound emission to open the haematoencephalic barrier and enhance drug diffusion in the area of the brain to treat can be monitored and synchronized according to the method of the invention as schematically represented in FIG. 6.

Figure 6:
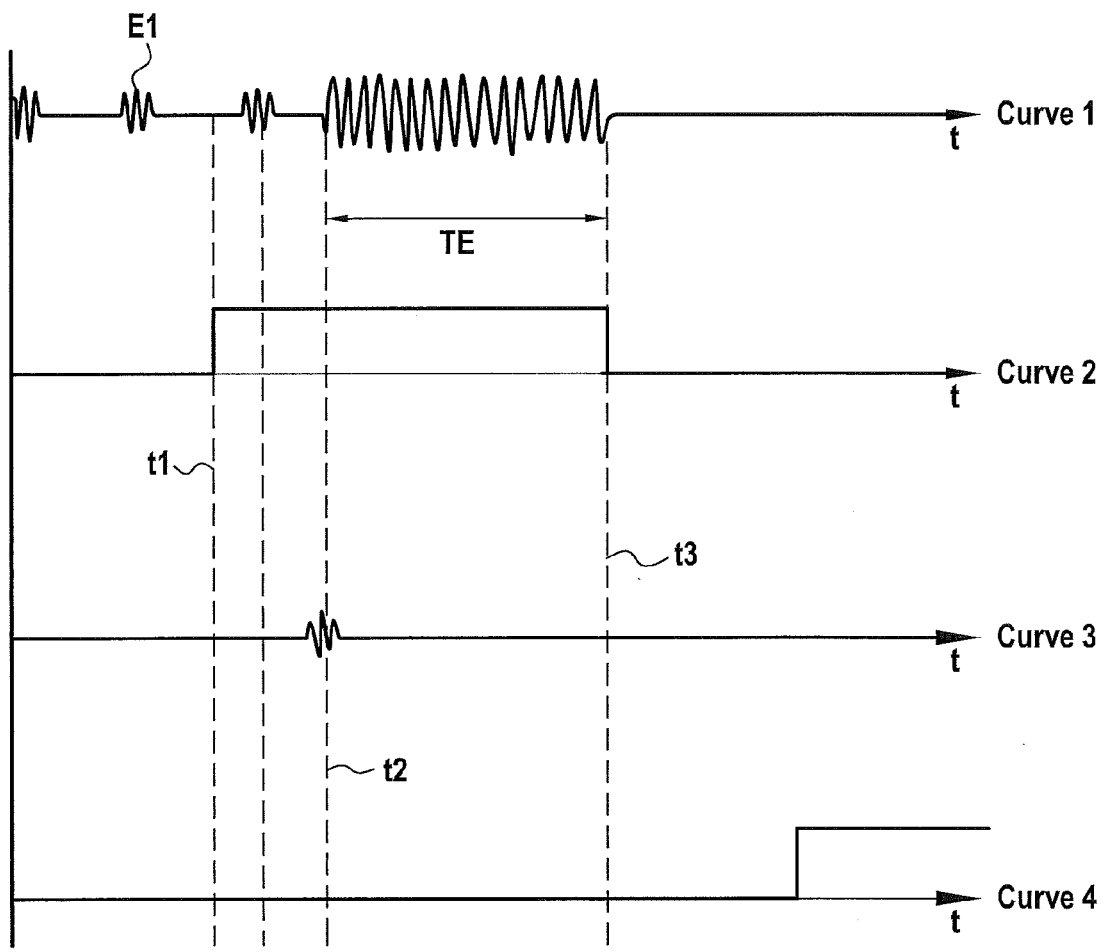
FIG. 6 represents schematically a treating sequence of a patient's brain area monitored and synchronized according to the method of the invention.

As shown in FIG. 6, the power controller PwC of the apparatus 1 of the invention drives short ultrasound waves emission E1 for echo-imaging at a pre-set frequency (curve 1). Then injection of contrast agent A is triggered at a time t1 by the power controller PwC (curve 2). The injection of contrast agent A causes diffusion of that agent A into brain's blood of the treated patient, which is detected at time t2 by the power controller PwC by reception of an echography signal (curve 3) generated by reflection of ultrasound waves emitted in the brain by the bubbling or constituents of the contrast agent A. This detection of the echography signal then triggers automatically a continuous emission of ultrasounds during an emission period TE (curve 1) to induce opening of the haematoencephalic barrier of the brain and ultrasound transmission to the area to treat. The injection of contrast agent A is maintained during the whole ultrasound emission period TE (curve 2). Then, once ultrasound emission and contrast agent A injection is terminated at a time t3, injection of chemotherapeutic drug B is commanded by the PwC (curve 4). Such monitoring and synchronisation further enhances the benefits of the combination of ultrasound waves stimulation of the area of the brain to treat and of the chemotherapeutic drugs.

Moreover, the apparatus and method of the invention consisting in ultrasound emission can also be applied for other medical application than tumor and cancer treatment. It can further be applied to induce a loco regional release of ultrasound sensible release/carrier agents such as nanoparticles, or liposomes for example. Still preferably, if the drug injected in the patients body is MRI-visible, its release within the brain can advantageously be monitored by MRI during or after the ultrasound emission treatment according to the method of the invention after connection of the implantable generator 4 of the apparatus of the invention to its power controller PwC. Such MRI monitoring is possible with the apparatus and methods of the invention as the implantable generator 4 doesn't contain any ferromagnetic material and the transdermic needles 19 used as connecting mains are coated with an isolating material.

The apparatus 1 and method of the invention have been thoroughly tested to demonstrate their feasibility and efficiency with animal subjects as described below and in reference to FIG. 7.

Tests were performed on ten healthy New-Zeland 4 kg rabbits, under general anaesthesia performed with Ketamine Imalgène®, Merial 1000 mg/10 ml and Xylazine Rompun®.

A 10 mm diameter craniotomy burr hole was performed. In that burr-hole an implantable generator comprising a mono element 1.05 MHz piezo composite treating device prototype was placed on the dura-matter of the rabbits brains.

Then ultrasound contrast agent (Sonovue®, Bracco, Italie) was intravenously injected (0.3 cc). Sonication was performed with the treating device on a pulsed fashion with a pulse duration of 25 millisecond, an electric tension of 90 mV leading to a tissue acoustic pressure of 0.55 MPa at 15 mm distant from the implantable generator. Sonication duration was 120 seconds starting at the end of the ultrasound contrast agent injection and Evans bleu (400 mg in 6.5 cc) was intravenously injected 30 minutes after sonication.

The rabbit sacrifice was performed (20 cc of 54.7 mg/100 cc Pentobarbital) 280 minutes after Evans bleu injection, and the brain was then extracted.

Figure 7:
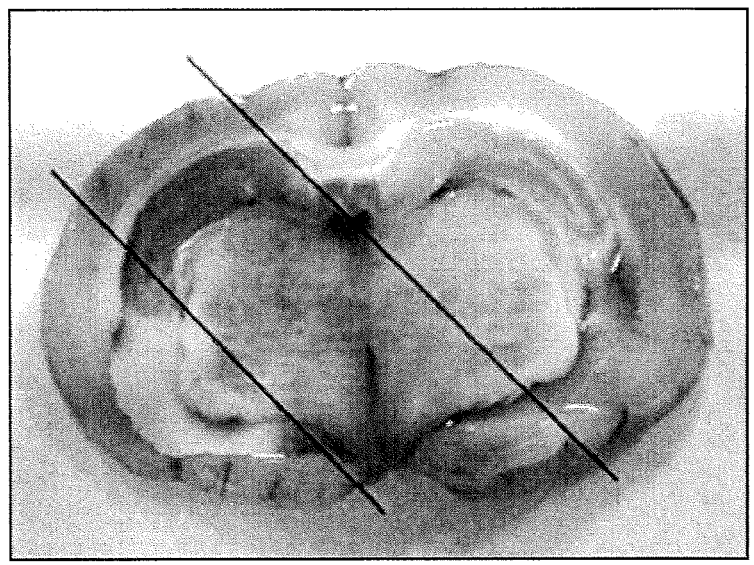
FIG. 7 represents a rabbit brain's slice after treatment with the apparatus of FIG. 1 and according to the method of the invention.

Macroscopic slices were performed and one slice is shown in FIG. 7, where the sonicated area is represented by parallel lines.

A clear diffusion of Evans Bleu was noticed in the interstitial brain tissue, exactly where the brain has been sonicated, meaning that the blood brain barrier has been successfully opened in this region (dark grey tissue coloration between the two added lines showing the ultrasounds emission band on FIG. 7). In parts of the brain that didn't received ultrasound emission, there is no Evans Bleu diffusion. No haemorrhagic suffusion occurred.

This set of experiments clearly proves that the tested prototype even with low power and non-focused ultrasound emission can effectively open the haematoencephalic barrier on a large region.

The implantation of the prototype within the bone thickness (prototype inserted in a burr-hole craniotomy) is a key condition for such results, since it solves the problem of bone ultrasounds absorption.

The invention claimed is:

1. Apparatus for the treatment of a brain affection, in particular brain tumor, characterized in that it comprises at least one MRI compatible implantable generator (2) made of non-ferromagnetic material for implantation into a burr-hole (3) performed in the skull (1) of a patient, said implantable generator (4) comprising:
   a casing (7) having at least an upper wall (8), and a lower wall (9) connected together by a peripheral wall (10),
   an ultrasound generating treating device (11) positioned into said casing (7) to induce brain affection treatment by emission of ultrasound waves through its lower wall (9) into the brain (2), and
   means (5, 12,12') for fastening the implantable casing into the skull,
said apparatus further comprising:
   a power controller (PwC) to supply electricity to the treating device (11) of the implantable generator (4) and to set and control its working parameters, and
   connecting means (6) to connect the power controller and the treating device of the implantable generator;
   wherein said implantable generator (4) comprises connecting plugs (15) to accommodate the connecting means (6) and assure connection between the power controller (PwC) and the treating device (11), and the connecting plugs (15) further comprise transdermic plugs held into the upper wall (8) of the casing (7) of the implantable generator (4) and an isolating coating preventing contact with the patients skin, the connecting means (6) comprising transdermic needles (19) suitable for plugging into the connecting plugs (15) through the patient's skin, said transdermic needles being coated with an isolating material (21) except at a tip (22) thereof for contacting the treating device connectors through the connecting plugs.

2. Apparatus for the treatment of brain affections according to claim 1, characterized in that the power controller (PwC) is adapted for the treating device (11) to emit ultrasound waves with an emission frequency between 200 kHz and 10 MHz, and preferably 1 MHz.

3. Apparatus for the treatment of brain affections according to claim 1, characterized in that the treating device (11) comprises at least one ultrasound transducer (13,17).

4. Apparatus for the treatment of brain affections according to claim 1, characterized in that it comprises beam steering elements to direct propagation of the ultrasound waves in the brain to a targeted area or location.

5. Apparatus for the treatment of brain affections according to claim 4, characterized in that the beam steering elements comprise phase difference inducing electrical components implemented in the power controller (PwC) and/or the treating device (11).

6. Apparatus for the treatment of brain affections according to claim 4, characterized in that the beam steering elements are integrated or associated to the ultrasound transducer(s) (13, 17) of said treating device (11).

7. Apparatus for the treatment of brain affections according to claim 1, characterized in that the treating device (11) comprises at least one light emitter.

8. Apparatus for the treatment of brain affections according to claim 7, wherein the at least one light emitter is at least one laser electroluminescent diode.

9. Apparatus for the treatment of brain affections according to claim 1, characterized in that the lower wall (9) of the casing (7) is permeable to ultrasound and/or light waves.

10. Apparatus for the treatment of brain affections according to claim 1, characterized in that the lower wall (9) of the implantable casing comprises or defines at least one lens assembly (23) for the ultrasound waves emitted into the brain.

11. Apparatus for the treatment of brain affections according to claim 10, characterized in that the at least one lens assembly (23) is advantageously displaceable about a longitudinal axis (X-X') of the casing to allow adjustment of the focal length of the ultrasound and/or light waves into the brain (2).

12. Apparatus for the treatment of brain affections according to claim 1, characterized in that the lower wall (9) of the casing comprises an external surface covered with a soft material (24) of variable thickness to provide a continuous interface with the brain (2) or dura-matter in the skull for the propagation of ultrasound waves into the brain.

13. Apparatus for the treatment of brain affections according to claim 1, characterized in that it further comprises detection elements for receiving and analysing ultrasound waves reflected by the brain (2).

14. Apparatus for the treatment of brain affections according to claim 13, characterized in that said detection elements comprise ultrasound transducers (17) connected to the power controller (PwC) for treatment of an electric signal derived from the reflected ultrasound waves.

15. Apparatus for the treatment of brain affections according to claim 1, characterized in that said power controller (PwC) and said connecting means are implemented into said casing (7) and said power controller comprises wireless programmable means, such as ultrasound communication means.

16. Apparatus for the treatment of brain affections according to claim 15, characterized in that it comprises a transcutaneous wireless remote control for programming and setting said wireless programmable means.

17. Apparatus for the treatment of brain affections according to claim 1, characterized in that it further comprises multiplexing means for controlling and setting the treating device (11).

18. Apparatus for the treatment of brain affections according to claim 1, characterized in that said casing (7) is made of an isolating material.

19. Apparatus for the treatment of brain affections according to claim 1, characterized in that said fastening means comprises tabs (12) formed on the edge of the upper wall of said casing, the tabs comprising screw holes for receiving anchoring screws (5).

20. Apparatus for the treatment of brain affections according to claim 1, characterized in that said fastening means comprises a screwing thread (12') on an external surface of the peripheral wall of the casing for said casing to be screwed manually in a burr-hole in the skull.

21. A method for treating brain affections, characterized in that it comprises the steps of:
performing at least one burr-hole (3) into the skull (1) of a patient,
implanting into said at least one burr-hole an implantable generator (4) of an apparatus for treating brain affections according to claim 1,
surgically close the skin and let it heal,
when needed for a treatment procedure, activating the implantable generator (4) and the power controller (PwC) of said apparatus,
supplying power to said generator to activate the treating device (11) of said generator and induce ultrasound waves emission into the brain (2),
treating an area of the brain located beneath the implantable generator by ultrasound waves emission into the brain during a determined period, and
deactivating the treating device when treatment is complete, wherein at least one contrast agent is injected into the patient's blood before and/or during ultrasound emission into the brain.

22. A method according to claim 21, characterized in that the treating device of the implantable generator comprises a light emitting device and focused or non-focused light waves are transmitted together with ultrasound waves in the brain for treating brain affections.

23. A method according to claim 21, characterized in that it further includes a step of intravenously injecting a drug in the patient's blood before or during ultrasound emission in the brain, said drug comprising therapeutic agents coated with ultrasound sensitive release/carrier agents, and then emitting in the brain with ultrasound waves transmitted with the implantable generator into the brain once the drug treatment has diffused in the patient's blood to release the therapeutic agents only into the area of the brain to be treated.

24. A method according to claim 23, characterized in that definitive or reversible sonoporation of the underneath cerebral tissue is carried out by ultrasound emission to increase drug input.

25. A method according to claim 23, characterized in that ultrasound waves emission and injection of one or both of the at least one contrast agent and drug is monitored and synchronized by means of the power controller of said apparatus for treating brain affections.

26. A method according to claim 23, characterized in that one or both of said at least one contrast agent and drug injected in the patient's body is MRI-visible and its release within the brain is monitored by MRI during the ultrasound emission treatment.

27. A method according to claim 21, characterized in that ultrasound waves emission and injection of the at least one contrast agent is monitored and synchronized by means of the power controller of said apparatus for treating brain affections.

28. A method according to claim 21, characterized in that ultrasound emission induces a loco regional release of ultrasound sensible release/carrier agents such as nanoparticles or liposomes for example.

29. A method according to claim 21, characterized in that said at least one contrast agent injected in the patient's body is MRI-visible and its release within the brain is monitored by MRI during the ultrasound emission treatment.

30. A method according to claim 21, characterized in that modification of electrophysiological brain activity by mechanical shear stress, sonoporation, or hyperthermia is carried out by ultrasound emission.

31. A method according to claim 21, characterized in that a loco regional sono-destruction/decomposition of pathological abnormal molecular deposit is carried out by ultrasound emission.

32. A method according to claim 21, characterized in that the axis of the burr-hole pierced in the patients skull is directed towards a tumor to be treated in the brain.

33. A method according to claim 21, characterized in that several burr-holes are drilled in the patient's skull, each accommodating an implantable generator, said holes and generators being positioned in a specific fashion with regard to the area of the brain to be treated.

34. A method according to claim 21, characterized in that positioning of the burr-hole(s) and implantable generator(s) is carried out by stereotaxy.

35. A method according to claim 21, characterized in that the positioning of implantable generator(s) is performed at the end of a regular tumor debulking open head neurosurgical procedure, by using existing craniotomy burr hole(s).

\* \* \* \* \*